United States Patent
Praefke et al.

(10) Patent No.: US 8,269,050 B2
(45) Date of Patent: *Sep. 18, 2012

(54) PROCESS FOR PREPARING ETHYL TERT-BUTYL ETHER FROM TECHNICAL MIXTURES OF C4 HYDROCARBONS

(75) Inventors: Jochen Praefke, Oer-Erkenschwick (DE); Armin Rix, Marl (DE); Silvia Santiago Fernandez, Oviedo (ES); Matthias Groemping, Kenner, LA (US); Frank Hoeper, Haltern am See (DE); Udo Peters, Marl (DE); Joerg Leistner, Haltern am See (DE); Franz Nierlich, Marl (DE); Dirk Roettger, Recklinghausen (DE)

(73) Assignee: Evonik Oxeno GmbH, Marl (DE)

( * ) Notice: Subject to any disclaimer, the term of this patent is extended or adjusted under 35 U.S.C. 154(b) by 894 days.

This patent is subject to a terminal disclaimer.

(21) Appl. No.: 11/614,275

(22) Filed: Dec. 21, 2006

(65) Prior Publication Data

US 2007/0203369 A1 Aug. 30, 2007

(30) Foreign Application Priority Data

Dec. 28, 2005 (DE) .................. 10 2005 062 722

(51) Int. Cl.
 *C07C 41/06* (2006.01)
(52) U.S. Cl. ..................... 568/697; 568/690
(58) Field of Classification Search .......... None
 See application file for complete search history.

(56) References Cited

U.S. PATENT DOCUMENTS

| 3,846,088 | A | * | 11/1974 | Brown et al. ............. 44/449 |
| 4,161,496 | A | | 7/1979 | Humbert et al. |
| 4,448,643 | A | * | 5/1984 | Lindner et al. ............ 203/34 |
| 5,254,748 | A | * | 10/1993 | Hensley et al. ........... 568/697 |
| 6,472,568 | B1 | | 10/2002 | Marion et al. |
| 6,657,090 | B2 | | 12/2003 | Rix et al. |
| 7,002,053 | B2 | | 2/2006 | Nierlich et al. |
| 2006/0135833 | A1 | | 6/2006 | Malzkorn et al. |
| 2006/0264681 | A1 | | 11/2006 | Obenaus et al. |
| 2007/0203369 | A1 | | 8/2007 | Praefke et al. |
| 2010/0081562 | A1 | | 4/2010 | Lansink Rotgerink |
| 2011/0118523 | A1 | | 5/2011 | Winterberg et al. |

FOREIGN PATENT DOCUMENTS

| DE | 25 21 964 A1 | 11/1975 |
| DE | 103 34 001 A1 | 2/2005 |
| EP | 0 071 032 A1 | 2/1983 |
| WO | WO 97/32838 | 9/1997 |

OTHER PUBLICATIONS

U.S. Appl. No. 11/624,823, filed Jan. 19, 2007, Rix, et al.
U.S. Appl. No. 11/521,460, filed Sep. 15, 2006, Rix, et al.
U.S. Appl. No. 11/610,801, filed Dec. 14, 2006, Fernandez, et al.
U.S. Appl. No. 11/838,340, filed Aug. 14, 2007, Winterberg, et al.
U.S. Appl. No. 11/839,604, filed Aug. 16, 2007, Winterberg, et al.
U.S. Appl. No. 11/758,285, filed Jun. 5, 2007, Winterberg, et al.
U.S. Appl. No. 13/381,676, filed Feb. 28, 2012, Boeing, et al.
U.S. Appl. No. 13/381,680, filed Feb. 14, 2012, Winterberg, et al.

* cited by examiner

*Primary Examiner* — Rosalynd Keys
(74) *Attorney, Agent, or Firm* — Oblon, Spivak, McClelland, Maier & Neustadt, L.L.P.

(57) ABSTRACT

The invention relates to a process for preparing ETBE from technical mixtures which comprise at least 1-butene, isobutene, n-butane and 2-butenes, by reacting the isobutene present, distillatively removing a fraction comprising 1-butene and isobutene and again reacting the isobutene present therein to give ETBE.

22 Claims, 4 Drawing Sheets

PROCESS FOR PREPARING ETHYL TERT-BUTYL ETHER FROM TECHNICAL MIXTURES OF C4 HYDROCARBONS

CROSS REFERENCE TO RELATED APPLICATION

This application claims priority to German Patent Application No. 102005062722.6, filed on Dec. 28, 2005, which is incorporated herein by reference in its entirety.

FIELD OF THE INVENTION

The invention relates to a process for preparing ethyl tert-butyl ether (ETBE) from technical mixtures of $C_4$ hydrocarbons which comprise at least 1-butene, isobutene, n-butane and 2-butenes.

DISCUSSION OF THE BACKGROUND

1-Butene, as well as other $C_4$ hydrocarbons (such as isobutene and 2-butenes) are obtained in large amounts from technical $C_4$ cuts, for example the $C_4$ cut from steamcrackers or FCC units. These $C_4$ cuts comprise butadiene, the monoolefins isobutene and 1-butene, the two 2-butenes, and also the saturated hydrocarbons isobutane and n-butane. Owing to the low boiling point differences of the ingredients and their low separation factors, a distillative workup is difficult and uneconomic. Linear butenes and other products are therefore usually obtained by a combination of chemical reactions and physical separating operations.

The first step in obtaining ethyl tert-butyl ether, which is common to all workup variants, is frequently the removal of most of the butadiene. The butadiene is removed by extraction, extractive distillation, or it is hydrogenated selectively to linear butenes down to a residual concentration of approximately 2000 ppm by mass. What remains, after any of these operations, is a hydrocarbon mixture (so-called raffinate I or hydrogenated crack-$C_4$). The raffinate I comprises the saturated hydrocarbons n-butane and isobutane, the olefins isobutene, 1-butene and the cis and trans 2-butenes.

Alkyl tert-butyl ether(s) (ATBE), in particular ethyl tert-butyl ether (ETBE) and methyl tert-butyl ether (MTBE), can be obtained by reacting the isobutene present in the raffinate I with an alcohol. After the conversion of the isobutene and removal of the alkyl tert-butyl ether, what remains is a hydrocarbon mixture (raffinate II). The raffinate II comprises the linear butenes and the saturated hydrocarbons isobutane and n-butane. This components of raffinate II can be separated further by distillation, for example into isobutane and 1-butene and a mixture of two 2-butenes and n-butane. In further distillation steps, 1-butene which contains only small amounts of isobutene can be obtained in high purity from the 1-butenic fraction. Highly pure 1-butene is desirable because 1-butene is used to a large degree as a comonomer in ethylene polymerization, where isobutene contaminations are undesired. Typical specifications of 1-butene therefore restrict the content of isobutene in the 1-butene to below 2000 ppm. Processes for preparing ATBE from $C_4$ hydrocarbon fractions comprising isobutene therefore have high economic viability, especially when the ATBE can be prepared without large losses of 1-butene.

For the reaction of isobutene with alcohols, for example methanol or ethanol, to give the corresponding tertiary butyl ethers, several process technology variants have been developed. The technique of reactive distillation has been found to be particularly useful for achieving high isobutene conversions.

Industrially, the most important process is the reaction of isobutene with methanol to give methyl tert-butyl ether (MTBE). Methyl tert-butyl ether is used mainly as a fuel additive. Because of the ever greater availability of ethanol from renewable raw materials, the demand for ETBE as a fuel additive is also increasing.

EP 0 048 893 describes a process for coproducing isobutene oligomers and alkyl tert-butyl ether (ATBE), from $C_4$ cuts, in one reactor. The process employs a catalyst. The catalyst is an acidic ion exchange resin which has been partly modified with metals of the seventh and eighth transition Groups of the Periodic Table of the Elements. After the catalytic reaction, the isobutene oligomers and alkl tert butyl ether, and the unconverted $C_4$ hydrocarbons, are separated by distillation. In this process, approximately 8% of the linear butenes are lost by oligomerization. The loss of 1-butene is 7%. However, the main disadvantage of this process is that full isobutene conversion is not achieved, resulting in an isobutene content, in the distilled $C_4$ hydrocarbon fraction, that is too high to obtain on-spec 1-butene therefrom.

DE 25 21 964 describes a two-stage process for preparing alkyl tert-butyl ethers. In the first stage, isobutene is reacted with alcohol for form an ether, and the ether is removed from the product mixture of the first stage. The remaining residue of the product mixture is conducted into a second reaction stage in which remaining isobutene is again reacted with alcohol.

U.S. Pat. No. 4,797,133 describes a process wherein initially, the isobutene content of the starting hydrocarbon stream is reduced, for example by reacting isobutene to give methyl tert-butyl ether (MTBE), and the methyl tert-butyl ether is then removed. The remaining residue of the starting hydrocarbon stream is subsequently fed to an etherification stage in which the remaining isobutene is converted.

EP 0 071 032 likewise describes a two-stage process for preparing ETBE in which the ETBE formed in the first stage is removed from the reaction mixture between the first and second stage.

A disadvantage of all of these processes is the large amounts of material which have to be conducted into the second reaction step.

SUMMARY OF THE INVENTION

It is therefore an object of the invention to provide an improved process for preparing ETBE as a fuel additive.

BRIEF DESCRIPTION OF THE DRAWINGS

A more complete appreciation of the invention and many of the attendant advantages thereof will be readily obtained as the same become better understood by the reference to the following detailed description when considered in connection with the accompanying drawings, wherein The process according to the invention will be illustrated in detail below with reference to the figures FIG. 1 to FIG. 5 and FIG. 8, without any intention that the process be restricted to the embodiments depicted there by way of example. The figures

FIG. 1 shows an embodiment of the invention for obtaining ethyl tert-butyl ether. In the process, a technical mixture of $C_4$ hydrocarbons is introduced into stage (a). In stage (a), some of the isobutene present in the technical mixture is reacted with ethanol. The product of stage (a) is transferred into the separation stage (b) in which unconverted $C_4$ hydrocarbons III and any ethanol present in excess are removed from the ETBE II. The separation is preferably a thermal separation. The unconverted $C_4$ hydrocarbons III are transferred into a stage (c) which can be realized, for example, by a simple distillation column. In this column, stream III is separated into a fraction IV which comprises isobutene, isobutane and 1-butene, and an isobutene-free or virtually isobutene-free fraction V which comprises 2-butenes and n-butanes. Fraction IV is transferred into the second reaction stage (d) in which the isobutene is reacted with ethanol again to give ETBE VII. In a subsequent separation stage (e), the ETBE VII is separated from unconverted hydrocarbons VIII. These hydrocarbons VIII are transferred into stage (i) in which the 1-butene is separated by distillation from the remaining hydrocarbons.

FIG. 2 shows a schematic diagram of a possible embodiment of process steps a) and b). The technical mixture I is first conducted into a first etherification reactor R-a1. The product from the first reactor is conducted into a second etherification reactor R-a2 (method with identical or different temperature possible). The effluent from the second etherification reactor is transferred into a distillation column K-b1 which is equipped with a condenser W-b2 for the top product and a bottom evaporator W-b1. A portion of the top product is returned into the column as reflux. The top product removed is the stream III which comprises unconverted $C_4$ hydrocarbons, and the bottom product obtained is the product II from the reaction of the isobutene, which consists principally of ETBE.

FIG. 3 shows a schematic diagram of a further possible embodiment of process steps a), b) and f. The technical mixture I is fed into the first reactor R-a1, of a battery of two reactors. Ethanol is also fed into the reactor R-a1. The reactor R-a1 has a recycle line with which a portion of the reactor effluent can be returned into the feed stream to the reactor. The other portion of the reactor effluent from reactor R-a1 is conducted into the second reactor R-a2. The effluent from the second reactor is conducted into a distillation column K-b1 which is equipped with a condenser W-b2 for the top product, and a bottom evaporator W-b1. A portion of the top product is returned as reflux into the column. The bottom product obtained is the product II, principally ETBE, with or without residual amounts of ethanol. The top product removed is the stream D-b1 which comprises unconverted hydrocarbons, with or without ethanol. When the stream comprises ethanol, this stream can be conducted into the bottom of an extraction column K-f2, into which an extractant, for example water, is fed in countercurrent via the feed E-f1 disposed at the top and is withdrawn via the outlet E-f2 at the bottom of the column. At the top of the column, the product obtained from the extraction is the stream of hydrocarbons III unconverted in stage (a).

FIG. 4 shows one possible embodiment of stages c), d), e) and h). The hydrocarbon stream III from stage b) is fed into a distillation column K-c1 which is equipped with a bottom evaporator W-c1 and, at the top, with a condenser W-c2 and a decanter, and is separated into a (virtually) isobutene-free fraction V comprising 2-butenes and n-butanes which is removed at the bottom of the column, and a fraction IV which comprises isobutene and 1-butene, is virtually free of n-butane and 2-butenes and is optionally separated in a decanter from an aqueous phase D-c1. A portion of the top product reduced by the aqueous fraction can be returned into the column as reflux. Fraction IV is transferred into the reactor R-d1, into which ethanol is also fed and in which the isobutene present in fraction IV is converted to ETBE (stage d)). The effluent from reactor R-d1 is fed into a column K-e1 which can be designed as a simple distillation column or, as shown here, as a reactive column. The effluent from the reactor is fed into the reactive distillation column K-e1 preferably below the reactive packing. The column K-e1 is equipped with a bottom evaporator W-e1 and a condenser W-e2 for the top product. The bottom product obtained from the column K-e1 is a stream comprising ETBE. The top product D-e1 can be returned partly as reflux into the column. The other portion is transferred into an extraction column K-h2, into which an extractant, for example water, is fed in countercurrent via the feed E-h1 disposed at the top and is withdrawn via the outlet E-h2 at the bottom of the column. At the top of the column, the product obtained from the extraction is the stream of hydrocarbons unconverted in stage d) and, where present, e), VIII.

FIG. 5 shows a schematic of one possible embodiment of process step i). The hydrocarbon stream VIII from stage e) or h) is fed into a distillation column K-i1. Column K-i1 is equipped with a bottom evaporator W-i1 and a condenser W-i2 for the top product. The bottom product S-i1 obtained from the column K-i1 is 1-butene. The top product D-i1, from which water is optionally removed in a decanter, is returned partly as reflux into the column. The other portion of the top product D-i1 is transferred into the distillation column K-i2. This column K-i2 too is equipped with a bottom evaporator W-i3 and a condenser W-i4 for the top product. The bottom product S-i2 obtained from the column K-i2 is isobutane. The top product D-i2, from which water is optionally removed in a decanter, is returned partly as reflux into the column. The other portion of the top product D-i2, which consists predominantly of low boilers, can be fed to a further use or to a thermal utilization.

The isobutane obtained in this workup (stream S-i2) may still comprise fractions of unsaturated components, principally 1-butene. These fractions of unsaturated components be hydrogenated to the corresponding alkanes in a downstream hydrogenation. This hydrogenation is effected by known industrial processes, preferably in the liquid phase over a palladium catalyst.

Figure 5:
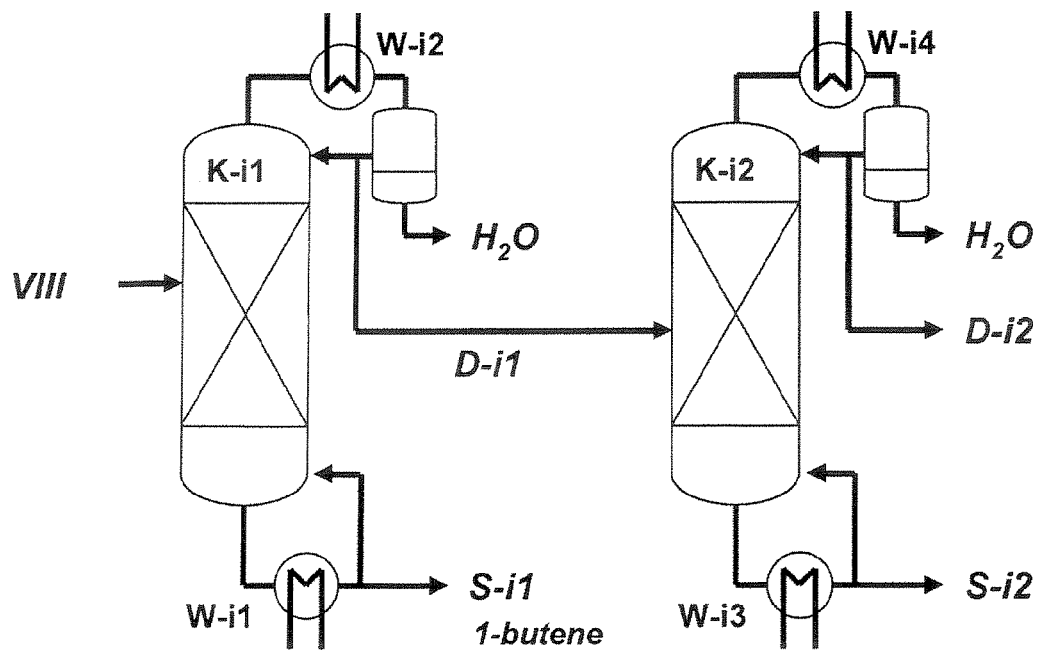
FIG. 5

Optionally, this hydrogenation may also be effected upstream of column K-i2; in this case, stream D-i1 is fed first to the hydrogenation (not shown in FIG. 5) and then to K-i2.

FIG. 6

Figure 3:
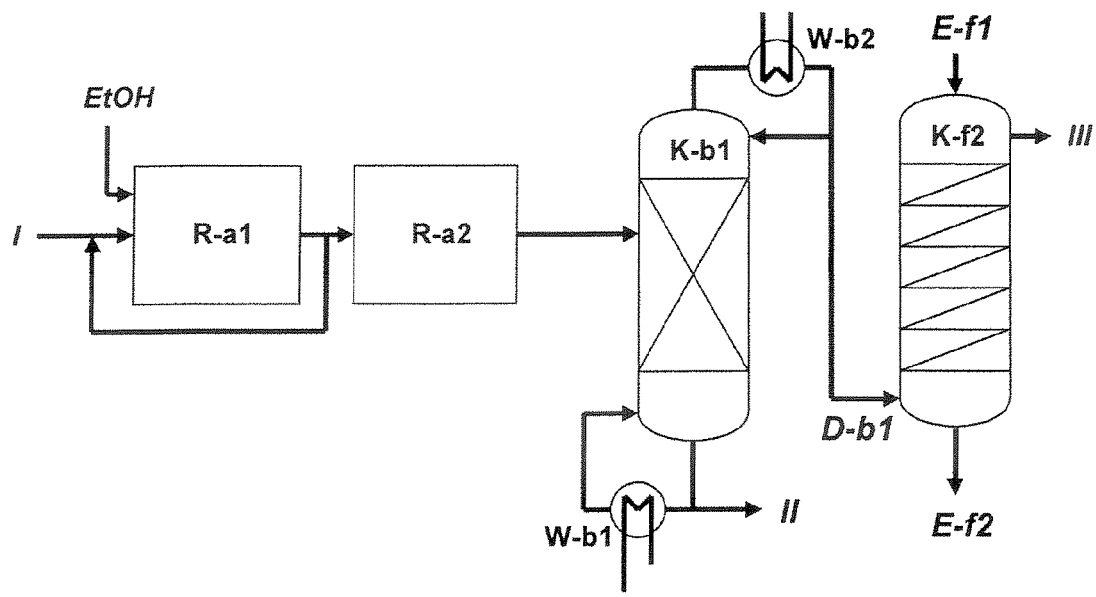
FIG. 3

This figure shows the variant A calculated in the comparative example of a one-stage process. In this variant, stages (a) and (b) are carried out in an arrangement as shown in FIG. 3, any desired reactor system R-a being present in place of reactors R-a1 and R-a2. The product III obtained at the top of the extraction column K-f2 is transferred into the distillation column K-c1 in which isobutane, isobutene and 1-butene are removed via the top. The bottom product S-c1 obtained is a (virtually) isobutene-free fraction V comprising 2-butenes and n-butanes. The distillate IV of column K-c1 is conducted directly into a further column K-i1 in which it is separated into a bottom product comprising 1-butene and a top product comprising isobutane and/or low boilers. The bottom product obtained is a 1-butene-rich fraction which, however, comprises the majority of the isobutene unconverted in R-a.

FIG. 7

Figure 1:
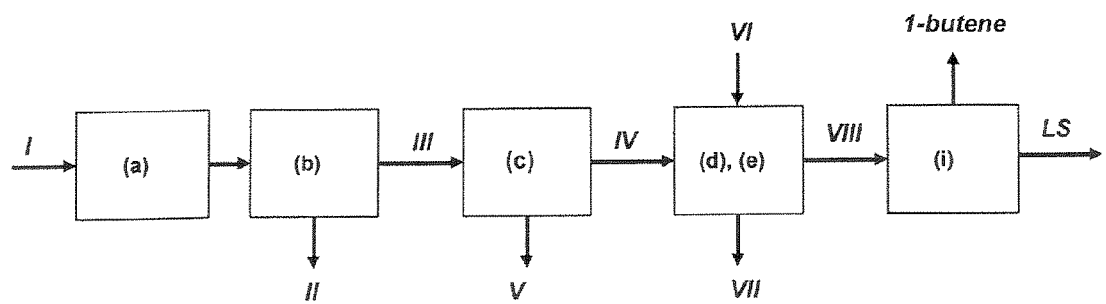
FIG. 1
Figure 2:
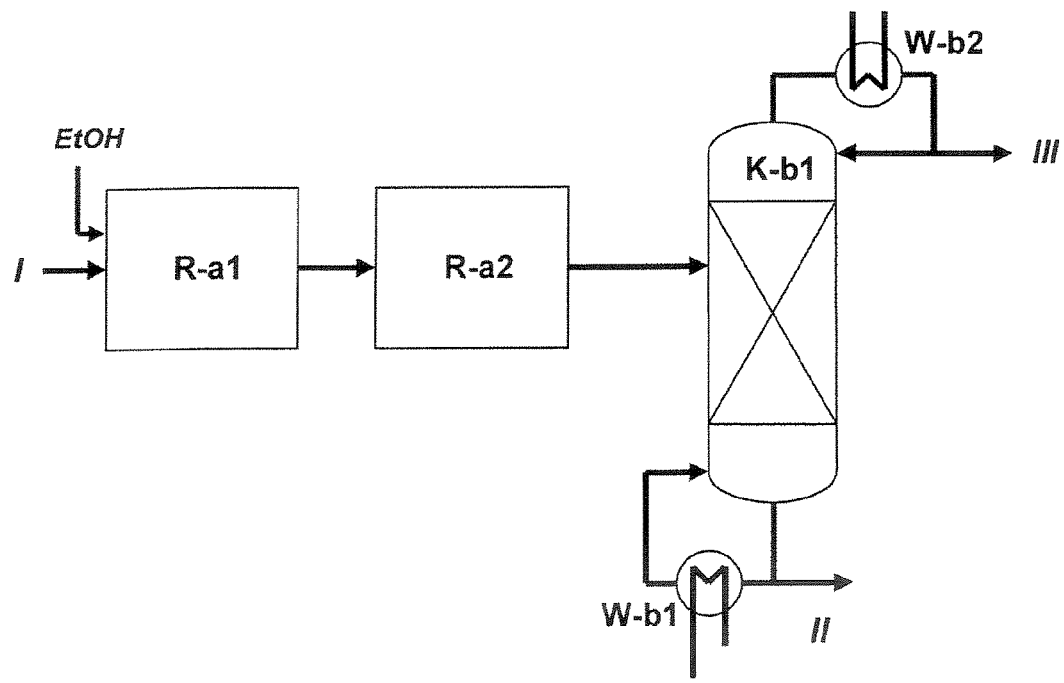
FIG. 2

This figure shows the variant B of a two-stage process calculated in the comparative example. In this variant, stages (a) and (b) are carried out in an arrangement as shown in FIG. 2, any desired reactor system R-a1 being present in place of reactors R-a1 and R-a2. The distillate D-b1 obtained from the column K-b1 is conducted directly into a second reactor R-b2 in which the residual isobutene present in the distillate D-b1 is reacted with the ethanol present and any ethanol added. The reaction product from the reactor R-b2 is conducted into a column K-b3 in which the ETBE formed in R-b2 is removed from the residual $C_4$ hydrocarbon stream D-b3 as the bottom product II. The further workup of the distillate D-b3 is effected as shown in FIG. 6 for the distillate D-b1.

FIG. 8

Figure 4:
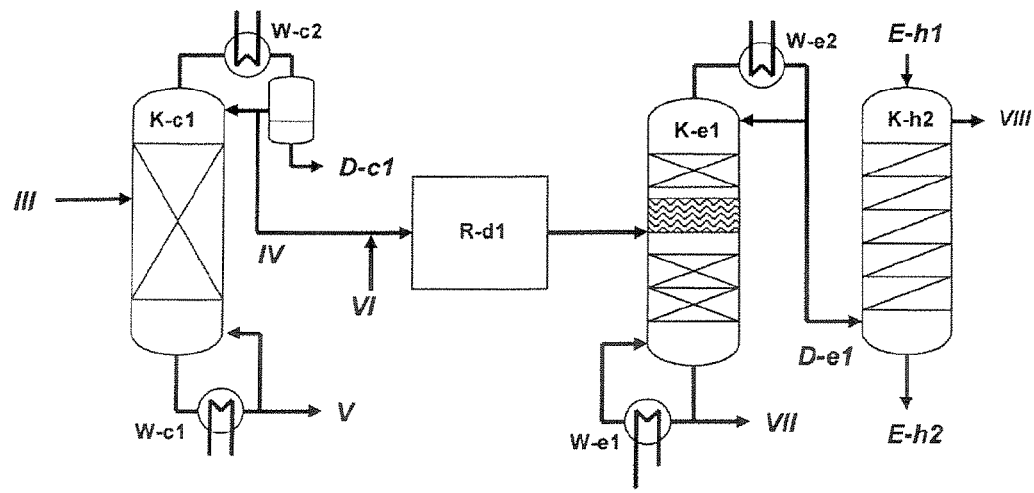
FIG. 4
Figure 6:
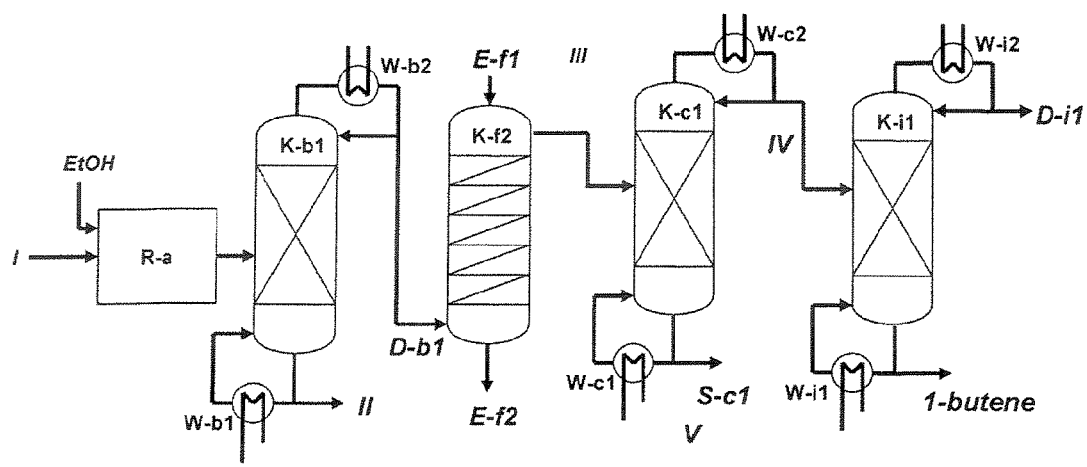
FIG. 6 and FIG. 7 show comparative variants. The schematic diagrams show only the essential stages. The illustration of streams customary for process technology purposes, for example cooling water streams, circulation streams or recyclings, and/or customary apparatus, for example heat exchangers or separators, has been dispensed with partly in favor of better clarity.
Figure 7:
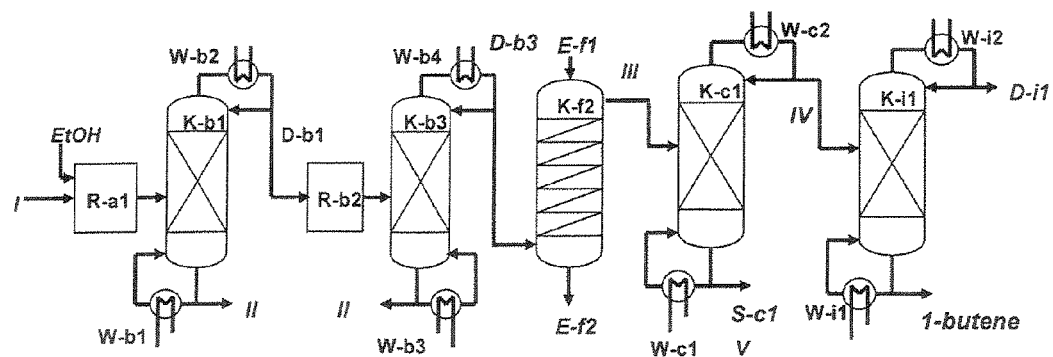
Figure 8:
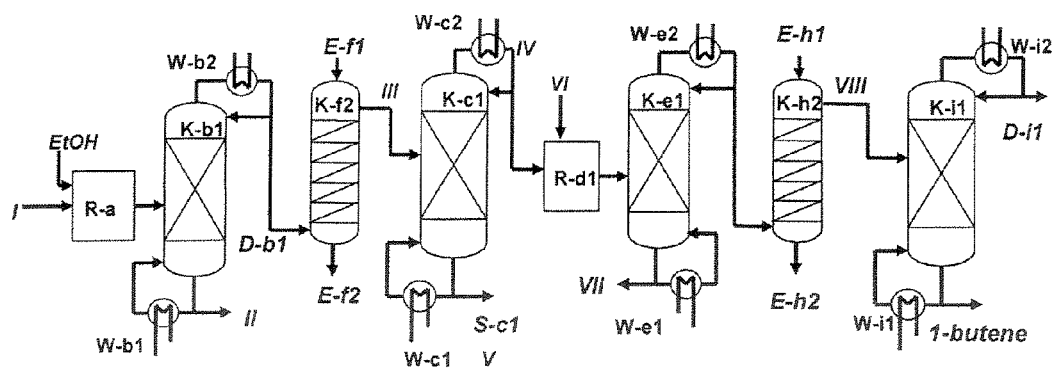

For better comparison of the arrangement according to the embodiment of the process according to the invention as has been used in the example in variant C with comparative variants A and B according to FIGS. 6 and 7, FIG. 8 shows a schematic of an arrangement in which an etherification step is carried out both in stage (a) and in stage (d). Stages (a) and (b) are carried out in an arrangement as shown in FIG. 3, one reactor system R-a being present in place of reactors R-a1 and R-a2. Stages (c), (d) and (e) are carried out as described in FIG. 4. The product VIII which is obtained from the extraction column K-h2 is conducted into the distillation column K-i1 in which it is separated into a bottom product comprising 1-butene and a top product comprising isobutane and/or low boilers.

DETAILED DESCRIPTION OF THE PREFERRED EMBODIMENTS

It has now been found that, surprisingly, ETBE can be prepared from a technical mixture of $C_4$ hydrocarbons, which comprise at least 1-butene, isobutene, n-butane and 2-butenes, in high yield and with a low level of complexity. The preparation of ETBE is effected in a two-stage reaction process. In the first stage, isobutene is reacted with ethanol to give ETBE. After the first stage is completed, the ETBE is removed and the remaining hydrocarbon stream is separated by distillation into a fraction comprising at least 2-butenes and n-butane and into a fraction comprising 1-butene and isobutene, with or without isobutene. The fraction comprising 1-butene and isobutene, with or without isobutene, is then conducted into a second etherification stage.

The present invention therefore provides a process for preparing ethyl tert-butyl ether (ETBE) from technical mixtures of $C_4$ hydrocarbons I which comprise at least 1-butene, isobutene, n-butane and 2-butenes, the process comprising
a) reacting portions of the isobutene present in the technical mixture with ethanol in the presence of an acidic catalyst to give ETBE,
b) removing the unconverted $C_4$ hydrocarbons III from the effluent of a) by a thermal separating process to obtain a fraction II comprising ETBE,
c) distillatively separating the $C_4$ hydrocarbons III into a fraction IV comprising at least 1-butene and isobutene, and a virtually isobutene-free fraction V comprising at least 2-butenes and n-butane,
d) reacting the isobutene present in fraction IV with ethanol VI in the presence of an acidic catalyst to give ETBE,
e) removing the unconverted $C_4$ hydrocarbons VIII from the effluent of stage d) to obtain a fraction VII comprising ETBE.

One particular advantage of the process according to the invention is that, as a result of removing the 2-butenes and n-butanes from the reaction mixture in c), a smaller volume stream has to be conducted through d). Because a smaller volume stream is conducted through d), the reactor(s) in d) can be designed on a relatively small scale or, with the same size in comparison to conventional processes, higher conversions can be achieved. A further advantage of the removal of the 2-butenes and n-butanes in c) is that the starting concentration of isobutene in d) is correspondingly higher, which simplifies the conversion of the isobutene in process d).

Another advantage of the process according to the invention is that, as a result of the reduced volume stream in d) and e), a distinctly smaller amount of energy, for example in the form of heat, has to be used in e).

The process of the invention is additionally attractive because bioethanol, which is a renewable source of ethanol, can be utilized for the preparation of ETBE, thus replacing MTBE, which is based on fossil raw materials.

The inventive process for preparing ETBE from technical mixtures of $C_4$ hydrocarbons I, which comprise at least 1-butene, isobutene, n-butane and 2-butenes, comprises
a) reacting a portion of the isobutene present in the technical mixture with ethanol, in the presence of an acid catalyst, to give ETBE,
b) removing the unconverted $C_4$ hydrocarbons III from the effluent of stage a) by thermal separation processes to obtain a fraction II comprising (substantially) ETBE,
c) distillatively separating the $C_4$ hydrocarbons III into a fraction IV containing at least 1-butene and isobutene, and a virtually isobutene-free fraction V containing at least 2-butenes and n-butane,
d) reacting the isobutene present in fraction IV with ethanol VI in the presence of acidic catalysts to give ETBE and
e) removing the unconverted $C_4$ hydrocarbons VIII from the effluent of stage d) to obtain a fraction VII comprising ETBE.

Process Step a)

a) is preferably carried such that the conversion of isobutene is greater than 50%, preferably greater than 70%, preferentially greater than 80%, more preferably greater than 90% and most preferably greater than 95%. The magnitude of the conversion of isobutene can be controlled, for example, by the number of reactors used in a) or by selection of suitable reaction conditions which the person skilled in the art can determine easily by simple preliminary experiments.

The etherification of the isobutene is carried out as an acid-catalyzed reaction. The ethanol used may be highly pure ethanol, pure ethanol or ethanol which has small amounts of impurities. The purity of the ethanol used, reported in % by mass of ethanol, is preferably greater than 90%, more preferably greater than 95% and most preferably equal to or greater than 99%. The ethanol which has a purity of greater than or equal to 99% by mass may be bioethanol. The content of water is preferably below 3% by mass, more preferably below 1% by mass, most preferably below 0.5% by mass. The alcohol can be dried by azeotropic distillation and/or membrane processes.

The ethanol is more preferably denatured ethanol. The ethanol is most preferably ethanol which has ETBE as a denaturing agent, preferably in a concentration of from 0 to 5% by mass, preferably from 0.005 to 1% by mass, more preferably from 0.05 to 1% by mass and most preferably from 0.01 to 0.2% by mass. In Germany, particular preference is given to using ethanol which has at least from 0.1 to 1% by mass of denaturing agent.

For the reaction of isobutene with alcohols, especially with methanol to give methyl tert-butyl ether, various process variants have been developed (cf.: Ullmann's Encyclopedia of Industrial Chemistry, Online Version, 2004, Wiley & Sons, under Methyl tert-butyl ether, and literature cited there; Obenaus, Fritz; Droste, Wilhelm, Erdoel & Kohle, Erdgas, Petrochemie (1980), 33(6), 271 to 275; DE 26 29 769; DE 28 53 769). In principle, all processes are suitable within the context of this invention for reacting portion of the isobutene with an alcohol as in a). Preference is given to processes in which the reaction is effected in the liquid phase over an acidic ion exchange resin.

The reactors in which the ethanol is reacted with the isobutene, up to close to the thermodynamic equilibrium, may be conventional fixed bed reactors (tube bundle reactors, adiabatic fixed bed reactors, circulation reactors, etc.). They may be operated with or without partial recycling, and the recycle stream may optionally be cooled.

In a preferred embodiment, the conversion of the isobutene is carried out in at least two stages, in which case the first stage is operated as an adiabatic fixed bed reactor with recycling (loop reactor) and the following stages as fixed bed stages without recycling and/or as a reactive distillation. The ratio of recycled amount to fresh feed ($C_4$ hydrocarbons and ethanol) is preferably from 0.5 to 20 t/t, more preferably from 1 to 5 t/t, and most preferably from 2 to 3 t/t. The reactors may be operated at temperatures of preferably from 10 to 160° C., preferentially from 30 to 110° C. The pressure in the fixed bed stages is preferably from 5 to 50 $bar_{abs}$ (bara), preferentially from 7.5 to 20 bara and more preferably from 8 to 13 bara. The circulation reactor preferably has an inlet temperature of from 35 to 50° C. and an outlet temperature of from 50 to 70° C. and is preferably operated at from 10 to 13 bara. Since the thermodynamic equilibrium between ethanol/isobutene and ether at low temperature is predominantly to the side of the ether, it is preferred when using a plurality of reactors to operate the first of the reactors at higher temperature (high reaction rate) than the following reactors (exploitation of the equilibrium position). In a), particular preference is given to using a reactor system which has three reactors connected in series. In this situation, the first reactor is operated as a loop reactor and the two reactors downstream are operated in straight pass. It may be advantageous when a plurality, preferably two of these reactor systems, are present in a), that in the event of repair work in one reactor, for example catalyst change, a) can be carried out further in the other reactor system without interruption of the process (albeit with halving of the throughput). In the case where the reactor system is composed of three reactors, the reactors are operated preferably at a temperature of from 30 to 80° C., preferably from 40 to 75° C., and a pressure of from 5 to 20 bara, preferably from 7 to 15 bara, the temperature in the reactors preferably falling from the first to the last reactor. The reactors downstream of the circulation reactor preferably have an inlet temperature of from 30 to 50° C. and an outlet temperature of from 35 to 45° C., and are preferably likewise operated at from 8 to 13 bara.

The molar ratio of ethanol to isobutene in a) is preferably from 5:1 to 0.9:1, preferably from 2:1 to 1:1 and more preferably from 1.2:1 to 1:1. Since a relatively low conversion of isobutene can be accepted in process step a), a lower ethanol excess may be advantageous in comparison to process step d).

In a preferred embodiment, the addition of the ethanol to the isobutene is carried out in the presence of an acidic catalyst such that at least one reaction stage is carried out as a reactive distillation. More preferably, the acid-catalyzed etherification in a) is carried out in at least two reaction stages, in which case preferably at least one, more preferably the last reaction stage is carried out as the reactive distillation. In the fixed bed reactor(s), a reaction mixture which is close to the thermodynamic equilibrium with regard to its isobutene, ethanol and ETBE concentration is first prepared over an acidic catalyst from the isobutenic technical hydrocarbon mixture I and ethanol. The conversion of the isobutene is preferably more than 90%. This mixture is fed into the reactive distillation column in the next/last reaction stage, where a further portion of the isobutene is converted to the ether. More preferably, process step a) is performed in a reactor system which has three reactors connected in series, preferably fixed bed reactors, of which the first is preferably operated in loop mode and the two downstream reactors in straight pass, and has a reactive distillation, the reactor effluent of the last of the reactors connected in series being conducted into the reactive distillation.

Depending on the pressure, the isobutene is reacted with ethanol to give the corresponding tert-butyl ether in the reactive distillation preferably in the temperature range from 40 to 140° C., preferably from 60 to 90° C., more preferably from 65 to 85° C. (temperature in the region of the column in which the catalyst is disposed. The bottom temperature of the column may be significantly higher). The reactive distillation column is preferably operated at pressures, measured at the top of the column, of from 3 bara to 15 bara, preferably from 7 bara to 13 bara, in particular from 8 bara to 11 bara.

When a) of the inventive process has a reactive distillation, the $C_4$ hydrocarbon mixture comprising isobutene is, as described in DE 101 02 082 for MTBE, fed together with ethanol into the first of the prereactors. In this case, the ethanol is preferably used in excess. In the prereactors, a mixture forms in which isobutene, ethanol and ETBE are present in equilibrium or virtually in equilibrium. This reaction mixture is introduced into the reactive distillation column.

In the feed of the reactive distillation column, more ethanol may be present than is needed for the full conversion of the isobutene still present. However, the ethanol excess should be such that a sufficient amount of ethanol is present for the azeotrope of ethanol and $C_4$ hydrocarbons.

The feeding to the reactive distillation column is preferably effected below the reactive packing, preferably from 3 to 13, more preferably from 4 to 10 theoretical plates below the reactive packing.

Optionally, when the ethanol content in the column feed to the reactive distillation column is below the maximum permissible value, additional ethanol can be added. In addition, ethanol feeding can be effected via a separate device at the top of the reactive distillation column above the column feed below a liquid distributor or in a liquid distributor above or in the region of the reactive zone, preferably in the region of the reactive zone. Additional feeding of ethanol can be effected, for example, into the reflux of the column or directly into the reactive packings. The ethanol addition should be such that, in the packings of the reactive zone, the ethanol content in the liquid phase is preferably greater than or equal to 1.5% by mass, preferentially greater than or equal to 2% by mass and more preferably from 2 to 3% by mass. The addition of ethanol into the reaction zone ensures that, in spite of the depletion, sufficient ethanol is available as a reactant.

The reactive distillation column above the catalyst packing preferably has a region of pure distillative separation, more preferably with from 5 to 20, in particular with from 7 to 10 theoretical plates. The catalyst zone can be estimated with a distillative action of from 1 to 5 theoretical plates per meter of packing height. The separation zone below the catalyst may preferably include from 12 to 36, in particular from 20 to 30 theoretical plates. The height of the catalyst zone/reactive zone can be determined by simple preliminary experiments as a function of the desired isobutene conversion. The amount of catalyst is preferably selected at such a level that an isobutene conversion of from 30 to 98%, preferably from 50 to 95% and more preferably from 75 to 90%, based on the isobutene content in the feed to the reactive distillation, is achieved.

The hydraulic loading in the catalytic packing of the column is preferably from 10% to 110%, preferably from 20% to 90% and more preferably from 35 to 75%, of its flood point loading. Hydraulic loading of a distillation column is understood to mean the uniform flow demand on the column cross section by the ascending vapor stream and the refluxing liquid stream. The upper loading limit indicates the maximum loading by vapor and reflux liquid, above which the separating action falls owing to entrainment or accumulation of the reflux liquid by the ascending vapor stream. The lower loading limit indicates the minimum loading, below which the separating action falls or collapses owing to irregular flow or emptying of the column—for example of the trays (Vauck/Müller, "Grundoperationen chemischer Verfahrenstechnik", p. 626, VEB Deutscher Verlag für Grundstoffindustrie). At the flood point, the shear stresses transferred from the gas to the liquid are so great that the entire amount of liquid is entrained with the gas in the form of drops, or that there is phase inversion in the column (J. Mackowiak, "Fluiddynamik von Kolonnen mit modernen Füllkörpern und Packungen für Gas/Flüssigkeitssysteme", Otto Salle Verlag 1991).

The reactive distillation column is preferably operated with reflux ratios less than 1.5, in particular with those which are greater than 0.6 and less than 1.2, preferably greater than 0.7 and less than 1.1.

The generic term "reactive distillation" includes all process technology measures in which distillation and reaction are carried out simultaneously. In the reactors described, this is achieved by particular design of the packings in a column. However, it is also possible in the inventive process to spatially separate these regions without dispensing with the advantages of a reactive distillation.

In one process variant, the reactive distillation column may be designed as a distillation column with one or more external reactors which contain the catalyst and are operated in a bypass stream, known as "side reactors."

The top product of the reactive distillation column comprises a $C_4$ hydrocarbon mixture and ethanol.

The catalyst in both the fixed bed stages and in any reactive distillation column present is preferably a solid substance which is soluble neither in the feedstock mixture nor in the product mixture and which has acidic sites on its surface. The catalyst should not release any acidic substances to the product mixture under reaction conditions, because this can lead to yield losses.

The activity of the catalysts is preferably selected such that they catalyze the addition of ethanol to isobutene under the reaction conditions but barely catalyze the addition to linear butenes. Moreover, the catalysts should as far as possible not catalyze, or only slightly catalyze, the oligomerization of linear butenes and dialkyl ether formation from two molecules of ethanol used. With regard to a high yield of 1-butene, the activity for the isomerization of 1-butene to 2-butene should preferably be low.

The solid catalysts used may, for example, be zeolites, acid-activated bentonites and/or aluminas, sulfonated zirconium oxides, montmorillonites or acidic ion exchange resins.

A group of acidic catalysts, which is preferred in the inventive process in a), is solid ion exchange resins, in particular those having sulfonic acid groups. Suitable ion exchange resins are, for example, those which are prepared by sulfonating phenol/aldehyde condensates or cooligomers of aromatic vinyl compounds. Examples of aromatic vinyl compounds for preparing the cooligomers are: styrene, vinyltoluene, vinylnaphthalene, vinylethylbenzene, methylstyrene, vinylchlorobenzene, vinylxylene and divinylbenzene. In particular, the cooligomers which are formed by reaction of styrene with divinylbenzene are used as a precursor for the preparation of ion exchange resins with sulfonic acid groups. The resins may be prepared in gel form, macroporous form or sponge form.

The properties of these resins, in particular specific surface area, porosity, stability, swelling, shrinkage, and exchange capacity can be varied by virtue of the preparation process.

In the inventive process, the ion exchange resins may be used in their H-form. Strongly acidic resins of the styrene-divinylbenzene type are sold, inter alia, under the following trade names: Duolite C20, Duolite C26, Amberlyst 15, Amberlyst 35, Amberlite IR-120, Amberlite 200, Dowex 50, Lewatit SPC 118, Lewatit SPC 108, K2611, K2621, OC 1501.

The pore volume is preferably from 0.3 to 0.9 ml/g, in particular from 0.5 to 0.9 ml/g. The particle size of the resin is preferably from 0.3 mm to 1.5 mm, in particular from 0.5 mm to 1.0 mm. The particle size distribution can be selected relatively narrowly or widely. For example, ion exchange resins with very uniform particle size (monodisperse resins) can be used. The capacity of the ion exchanger is, based on the supply form, preferably from 0.7 to 2.0 eq/l, in particular from 1.1 to 2.0 eq/l, or preferably from 0.5 to 5.5 mol/kg, in particular from 0.8 to 5.5 mol/kg (the capacity data in mol/kg each relate to the ion exchange resin dried to constant weight in a warm nitrogen stream at, for example, 105° C.).

In the reaction part of any reactive distillation present in a), the same catalysts may be used as are used in the simple reactors. In the reactive distillation column, the catalyst may either be integrated in the packing, for example KataMax® (as described in EP 0 428 265), KataPak® (as described in EP 0 396 650 or DE 298 07 007.3 U1) or polymerized on shaped bodies (as described in U.S. Pat. No. 5,244,929).

Process Step b)

In b), the unconverted $C_4$ hydrocarbons III are removed from the effluent of a) by thermal separation processes, for example by distillations or fractionations. When a) includes a reactive distillation, b) can take place partly or fully actually in the course of performance of the reactive distillation, and a separate b) can in some cases be dispensed with.

b) can preferably be carried out in a distillation column. The distillation column preferably has a number of theoretical plates of from 25 to 50, preferably from 30 to 40. The feed to this column is preferably in the region of the 10th to 15th theoretical plate (from the top). The distillation in a) is carried out preferably at a pressure of from 3 to 10 bara, preferably from 4 to 7 bara, a preferred top temperature of from 30 to 70° C., more preferably from 45 to 60° C., and a preferred bottom temperature of from 105 to 125° C., more preferably from 110 to 120° C.

The thermal separation process is preferably carried out such that the bottom product obtained is a fraction comprising ETBE and the top product obtained is a fraction containing unconverted $C_4$ hydrocarbons and ethanol. When the butene oligomers are removed before the reaction with ethanol, the bottom product of the reactive distillation column preferably comprises ETBE.

The top product of b), i.e. the top product of the reactive distillation or of the thermal separation, can be fed directly to a further separation in c) or else first be worked up in one or more workup steps.

Process Step f)

It may be advantageous when the inventive process, between b) and c), has a further step f) in which the ethanol is first removed fully or virtually fully from the unconverted $C_4$ hydrocarbons in the top product of b), i.e. the top product from the reactive distillation or from the thermal separation which comprises unconverted $C_4$ hydrocarbons and ethanol.

The top product from b), which is obtained at the top of the distillation column or reactive distillation column, is preferably transferred into an extraction column into which an extractant, for example water, is fed in countercurrent via a feed disposed at the top. The extractant can be withdrawn via the outlet at the bottom of the column. At the top of the column, the product obtained from the extraction is the stream composed of hydrocarbons III unconverted in a) and, if appropriate, b). This product can be fed into c).

f) can preferably be carried out in an extraction column. The extraction column preferably has from 5 to 20, preferentially from 10 to 15 theoretical plates. The extraction in f) is preferably carried out at a pressure of from 5 to 12 bara, preferably from 7 to 10 bara. The extraction in f) is preferably carried out at a temperature of from 30 to 60° C. and preferentially from 35 to 45° C. The ratio of extractant, preferably water, to the top product from process step b) or a) is preferably from 0.05 to 0.5, preferentially from 0.1 to 0.25 and more preferably from 0.15 to 0.2.

The ethanol-enriched extractant obtained in the bottom of the extraction column can be separated by distillation and the ethanol thus obtained, when water has been used as extractant, if appropriate after drying, can be fed back to the process as a starting material in a) or d).

Process Step c)

After removal of the ETBE, and optionally after removal of the unconverted ethanol, the hydrocarbon stream obtained from b) or f) is separated by distillation in c). The distillative separation is carried out in such a way as to obtain a fraction IV containing at least 1-butene and isobutene (top fraction) and a virtually isobutene-free fraction V (bottom fraction) containing at least 2-butenes and n-butane and preferably having less than 5% by mass, preferentially less than 1% by mass, and more preferably less than 0.1% by mass, of isobutene. Fraction V comprises at least 95% by mass, preferably at least 99% by mass, more preferably at least 99.8% by mass, of the 2-butenes originally present in the hydrocarbon stream obtained as the product of c). Fraction IV has preferably less than 1% by mass, more preferably less than 0.2% by mass, of n-butane. The distillative separation can be carried out in apparatus used customarily for the separation of such hydrocarbon mixtures. Such apparatus may, for example, be distillation or fractionation columns.

Fraction V may be used as an alkylating agent. In particular, it may be used as starting material for the preparation of n-butene oligomers, for example di-n-butene or tributene. An oligomerization process in which fraction V can be used is, for example, the OCTOL process of OXENO Olefinchemie GmbH, as described in DE 196 29 906 or EP 0 395 857.

Preference is given to carrying out the separation in a superfractionation column. The feed to this column is preferably in the lower half, preferably in the lower third of the column. Because of the narrow boiling point of the mixture to be separated, the distillation is preferably carried out in a column having preferably more than 100, preferentially more than 125, more preferably having 150 or more theoretical plates, and most preferably having 150 to 200 theoretical plates. The reflux ratio (reflux amount to distillate withdrawal) is, depending on the number of stages realized and on the operating pressure, preferably less than or equal to 20, preferentially less than or equal to 14, more preferably less than or equal to 11 and most preferably from 8 to 11. The condensation can be carried out against cooling water or air. The distillate vessel is preferably designed as a liquid-liquid separator. As a result, any water present in the feed stream can be removed as a second phase in the distillate vessel and a technical water-free bottom product can be obtained.

The separation in c) is preferably carried out at a pressure of from 4 to 10 bara, preferentially at a pressure of from 5 to 7 bara. The temperature at which the separation is carried out is preferably from 35 to 65° C., preferentially from 40 to 50° C.

To heat the evaporator of the column, it is possible to use a customary heat transferrer, for example steam or warm water, and also preferably waste heat from other processes. In the latter case, it may be advantageous to equip the column with more than one evaporator. The column is preferably equipped as a simple column with at least one evaporator and at least one condenser. Owing to the high energy demand and the small temperature difference between bottom and top of the column, energy-saving connections are particularly preferred embodiments. Reference is made here, by way of example, to the method of vapor compression. A further particularly preferred connection is two-pressure connection (double effect distillation) in integration with a second column. The second column may preferably be a parallel-connected column with the same or different separation task. In this case, one of the columns is operated at such high pressure that its condensation temperature is sufficient to heat the other column. In the connection of columns with different separation tasks for heating purposes, it is possible, in principle, to connect any suitable column from the inventive process, but also a column which is present at the plant site outside the inventive process, with the inventive column of c).

Process Step d)

In the inventive process, the isobutenic fraction IV obtained from c) is converted in a further reaction step (d) in which the remaining isobutene is converted by addition of ethanol to give ETBE.

Like the etherification in a), the etherification, in d), of the isobutene is carried out as an acid-catalyzed reaction. The ethanol used may be highly pure ethanol, pure ethanol or ethanol which has small amounts of impurities. The purity of the ethanol used, reported in % by mass of ethanol, is preferably greater than 90%, more preferably greater than 95%, and most preferably equal to or greater than 99%. Ethanol having a purity of greater than or equal to 99% by mass is supplied in Europe, for example, as bioethanol. The content of water is preferably below 3% by mass, more preferably below 1% by mass, most preferably below 0.5% by mass. In the inventive process, it may be advantageous to use denatured ethanol. The ethanol used is more preferably ethanol which has ETBE as a denaturing agent, preferably in a concentration of from 0 to 5% by mass, preferentially from 0.005 to 1% by mass, more preferably from 0.05 to 1% by mass and most preferably from 0.01 to 0.2% by mass. In Germany, preference is given to using ethanol which has from 0.1 to 1% by mass of denaturing agent. The use of ethanol denatured with ETBE prevents extraneous substances from being introduced into the process.

For the reaction of isobutene with alcohols, in particular with methanol to give methyl tert-butyl ether, various process variants have been developed (cf.: Ullmann's Encyclopedia of Industrial Chemistry, Online Version, 2004, Wiley & Sons, under Methyl tert-butyl ether, and literature cited there; Obenaus, Fritz; Droste, Wilhelm, Erdoel & Kohle, Erdgas, Petrochemie (1980), 33(6), 271 to 275; DE 26 29 769; DE 28 53 769). In principle, all known processes for reacting the isobutene with alcohols are suitable for use in d) within the context of the present invention.

Preference is given to using processes in which the reaction is effected in the liquid phase over an acidic ion exchange resin. The reactors used, wherein the ethanol is reacted with the isobutene up to close to the thermodynamic equilibrium, may be conventional fixed bed reactors (tube bundle reactors, adiabatic fixed bed reactors, circulation reactors). They may be operated with or without partial recycling, and the recycle stream may optionally be cooled. In d), particular preference is given to using a reactor system which has two reactors, in particular fixed bed reactors. Preference is given to operating the two reactors in straight pass.

The reactors may be operated at temperatures of from 25 to 110° C., preferably at temperatures of from 30 to 70° C., and more preferably at temperatures of from 35 to 50° C. The pressure is preferably from 5 to 50 bara, preferably from 10 to 20 bara and more preferably from 10 to 13 bara. Since the thermodynamic equilibrium between ethanol/isobutene and ether at low temperature is predominantly on the side of the ether, it is preferred in the case of use of a plurality of reactors to operate the first of the reactors at higher temperature (high reaction rate) than the following reactors (exploitation of the equilibrium position).

The molar ratio of ethanol to isobutene in the feed to d) is preferably in the range from 25:1 to 1:1, more preferably from 15:1 to 3:1, and more preferably in the range from 10:1 to 5:1.

The catalysts used may preferably be those as described for a), the inventive process being performable such that in each case the same catalyst or different catalysts may be used in a) and d). Preference is given to using the same catalyst in a) and d).

In a preferred embodiment, the addition of the ethanol to the isobutene is carried out in the presence of an acidic catalyst, such that at least one reaction stage is carried out as a reactive distillation. More preferably, the acid-catalyzed etherification in d) is carried out in at least two reaction stages, in which case preferably at least one, more preferably the last reaction stage, is carried out as the reactive distillation. In the fixed bed reactor(s), a reaction mixture which is close to the thermodynamic equilibrium with regard to its isobutene, ethanol and tert-butyl ether concentration is first prepared over an acidic catalyst from the isobutenic fraction IV and the ethanol VI. In this reaction step, the residual content of isobutene is preferably converted to such an extent that the required purity of the 1-butene can be achieved with the downstream reactive distillation. This mixture is fed into the next/last reaction stage in the reactive distillation column, where a further portion of the isobutene is converted to the ether. Most preferably, d) is carried out in a reactor system which has two reactors connected in series and a reactive distillation column, the two reactors preferably being operated in straight pass, and the effluent from the second reactor is fed into the reactive distillation column.

In the reaction part of the reactive distillation column, the same catalysts, as described above for the simple embodiment of the process stage without the use of a reactive distillation, may be used.

In the reactive distillation column, the catalyst may either be integrated in the packing, for example KataMax® (as described in EP 0 428 265), KataPak® (as described in EP 0 396 650 or DE 298 07 007.3 U1) or polymerized onto shaped bodies (as described in U.S. Pat. No. 5,244,929).

The reaction of the isobutene with ethanol to give ETBE is effected in the reactive distillation in the temperature range from 10 to 140° C., preferably from 30 to 70° C., more preferably from 35 to 50° C. (temperature in the region of the column in which the catalyst is disposed. The bottom temperature of the column may be significantly higher).

In particular, the ETBE is prepared by reaction with ethanol in a manner described in DE 101 02 082, for the reaction of methanol with isobutene to give MTBE. The $C_4$ hydrocarbon mixture comprising isobutene is fed into the prereactor(s) together with ethanol. The ethanol is preferably used in excess. In the prereactors, a mixture forms in which isobutene, ethanol and ETBE are in equilibrium or virtually in equilibrium. This reaction mixture is introduced into the reactive distillation column.

The feed to the reactive distillation column may comprise more ethanol than is needed for the full conversion of the isobutene still present. However, the alcohol excess should be such that a sufficient amount of ethanol is present for the azeotrope of ethanol and $C_4$ hydrocarbons which forms.

Optionally, for example when the ethanol content in the column feed is below the maximum permissible value, additional ethanol may be added to the column feed. In addition, ethanol feeding may be effected via a separate device at the top of the reactive distillation column above the column feed below a liquid distributor or in a liquid distributor above or in the region of the reactive zone, preferably in the region of the reactive zone. Additional feeding of ethanol can be effected, for example, into the reflux of the column or directly into the reactive packings. The additional ethanol addition should be such that the ethanol content in the liquid phase in the packings of the reactive zone is preferably greater than or equal to 1.5% by mass, preferably greater than or equal to 2% by mass, and more preferably from 2 to 3% by mass.

Preferably, the reactive distillation column has a region of pure distillative separation above the catalyst packing, more preferably having from 5 to 20, in particular having from 7 to theoretical plates. The catalyst zone can be estimated at a distillative action of from 1 to 5 theoretical plates per meter of packing height. The separation zone below the catalyst may preferably include from 12 to 36, in particular from 20 to 30 theoretical plates. The height of the catalyst zone/reactive zone can be determined by simple preliminary experiments depending upon the desired isobutene conversion. The amount of catalyst is preferably selected at such a level that a residual isobutene content in the top product of less than 2000 ppm by mass (ppmw), preferably less than 1500 ppmw, is achieved.

The feed to the reactive distillation column may be above or below the catalyst zone. The feed to the reactive distillation column is preferably below the reactive packing, preferably from 3 to 13, more preferably from 4 to 10, theoretical plates below the reactive packing.

The reactive distillation column is operated at pressures, measured at the top of the column, of from 3 bara to 10 bara, preferably from 4 bara to 7 bara, in particular from 5 bara to 6 bara. The hydraulic loading in the catalytic packing of the column is preferably from 10% to 110%, preferentially from 20% to 90% and more preferably from 35 to 75% of its flood point loading. The term "hydraulic loading" of a distillation column is understood to mean the uniform flow demand on the column cross section by the ascending vapor stream and the refluxing liquid stream. The upper loading limit indicates the maximum loading by vapor and reflux liquid, above which the separating action falls owing to entrainment or accumulation of the reflux liquid by the ascending vapor stream. The lower loading limit indicates the minimum loading, below which the separating action falls or collapses owing to irregular flow or emptying of the column—for example of the trays (Vauck/Müller, "Grundoperationen chemischer Verfahrenstechnik", p. 626, VEB Deutscher Verlag für Grundstoffindustrie.).

At the flood point, the shear stresses transferred by the gas to the liquid become so great that the entire amount of liquid is entrained in the form of drops with the gas or that there is phase inversion in the column (J. Mackowiak, "Fluiddynamik von Kolonnen mit modemem Füllkörpern und Packungen für Gas/Flüssigkeitssysteme", Otto Salle Verlag 1991).

The reactive distillation column is preferably operated with reflux ratios of from 0.2 to 4, in particular with those which are from 0.4 to 2, preferably from 0.5 to 1.

When a reactive distillation column is used as the last step in d), steps d) and also e), namely the removal of the ETBE from the unconverted hydrocarbons, can take place at least partly therein. It is then possible in some cases to dispense with a further step e).

The generic term "reactive distillation" includes all process technology measures in which distillation and reaction are carried out simultaneously. In the reactors described, this is achieved by a particular design of the packings in a column. In the inventive process, it is also possible to spatially separate these regions without dispensing with the advantages of a reactive distillation.

In one process variant, the reactive distillation column is designed as a distillation column with one or more external reactor(s) which contain(s) the catalyst and is/are operated in a bypass stream.

Process Step e)

When no reactive distillation column is used for etherification and simultaneous separation in d), a dedicated step e) has to be provided in the inventive process, in which the product from d) is separated into the ETBE-comprising bottom stream and a stream which comprises the unconverted hydrocarbons. Otherwise, the distillative separation is effected, as per e), in the reactive distillation column. The separation can be effected, for example, by feeding the effluent from the reactor of d) into a distillation column. The column can be equipped with a bottom evaporator and a condenser for the top product. The bottom product obtained from the distillation column is ETBE and in some cases excess ethanol. The top product can be returned partly as reflux into the column. The other portion can be fed to h).

The column has preferably more than 20, preferentially more than 25, more preferably from 30 to 50 theoretical plates. The reflux ratio is, depending on the number of stages realized, preferably less than or equal to 1. More preferably, the reflux ratio is set to a value of from 0.9 to 0.6. The condensation can be carried out against cooling water or air. To heat the evaporator of the column, steam, for example, can be used. It may be advantageous to pass the feed stream to the column in at least partly pre-evaporated form or to flash it directly into the column. For this purpose, heat is preferably supplied to the feed stream in an external heat transferrer, for example by utilizing waste heat. To achieve partial evaporation, a kettle evaporator is the preferred embodiment of the heat transferrer. It may also be advantageous when an intermediate evaporator heated to a low temperature level with process heat or waste heat is used in the lower section of the column.

In e), the feed to the column is preferably at the 10th to 15th theoretical plate. The column is preferably operated with a pressure of from 4 to 11 bara, preferably from 5 to 8 bara. The top temperature of the column used in e) is preferably from 40 to 70° C., preferentially from 45 to 60° C.

When the top product of e), irrespective of whether the step has been carried out in a distillation column or reactive distillation column, still has residual amounts of ethanol in the $C_4$ hydrocarbons, it may be advantageous to scrub them out with water in at least one additional extraction step. This scrubbing may be carried out by known standard industrial processes, for example in an extraction column or in a cascade of mixers and separating vessels (see process step h)).

The bottom product which contains ETBE and possibly excess ethanol may be used directly or sent to a workup, for example a further distillation, in which the ETBE is removed from the remaining constituents.

In a further preferred embodiment of the process, the bottom product obtained in the reactive distillation or distillation of d) or e), which comprises ETBE and unconverted ethanol if applicable, is returned fully or partly into a) and/or b). This embodiment is advantageous especially when the reaction in d) is operated with a stoichiometric excess of ethanol. In this variant, the reaction in d) is preferably carried out only in fixed bed reactors and a distillative separation in e) is preferably carried out in a distillation column. The unconverted $C_4$ hydrocarbons VIII are obtained as the top product, and the bottom product which is obtained and comprises at least ETBE and in some cases unconverted ethanol is returned fully or partly into a) and/or b). When d) is carried out with a large ethanol excess, for example with a molar ratio of ethanol to isobutene of greater than 2:1, in particular greater than 5:1, the bottom product obtained in e) is a mixture which comprises substantially ethanol and can therefore be returned particularly efficiently as a feedstock into a). In this embodiment, the ETBE is obtained exclusively as a bottom product of b). For distillative workup of the bottom product from e), process step b) is utilized in this embodiment.

Process Step h)

The top product from d) or e) which is obtained at the top of the distillation column or reactive distillation column is preferably transferred into an extraction column into which an extractant, for example, water, is fed in countercurrent via a feed disposed at the top. The extractant can be withdrawn via the outlet at the bottom of the column. At the top of the column, the product obtained from the extraction is the stream of hydrocarbons VIII unconverted in d) and, if appropriate, e). This can be sent to a further use, for example a workup to 1-butene (process step i)). The extractant which has been enriched with ethanol and is obtained in the bottom of the column can be separated by distillation and the ethanol, optionally after drying when water has been used as the extractant, can be returned to the process as the starting material in a) or d). This measure allows any downstream column (process step i)) to be operated at lower pressure. Without extraction, a downstream column would have to be operated at higher pressure in order to be able to remove ethanol via the top.

h) can preferably be carried out in an extraction column. The extraction column has preferably from 5 to 20, preferentially from 10 to 15 theoretical plates. The extraction in process step h) is carried out preferably at a pressure of from 5 to 12 bara, preferentially from 7 to 10 bara. The extraction in h) is preferably carried out at a temperature of from 30 to 60° C., more preferably from 35 to 45° C. The ratio of extractant, especially water, to the top product from d) or e) is preferably from 0.05 to 0.5, preferentially from 0.1 to 0.25, and more preferably from 0.15 to 0.2.

Process Step i)

1-Butene can be removed by distillation from the $C_4$ hydrocarbon mixture VIII of unconverted hydrocarbons obtained from the reactive distillation or distillation in e). The $C_4$ hydrocarbon mixture VII may have been freed of ethanol and comprises essentially 1-butene, isobutane and low boilers. The 1-butene is removed preferably by distillation of the mixture VIII in one or more distillation columns.

In a preferred embodiment, the 1-butene is removed in a distillation column in which the bottom product obtained is very pure 1-butene. The top product obtained is an isobutane-rich fraction which may additionally comprise low boilers (for example $C_3$ hydrocarbons).

The separation is preferably carried out in a superfractionation column. The feed to this column is preferably into the upper half, preferentially into the lower half of the upper half of the column. Owing to the narrow boiling point of the mixture to be separated, the column is designed with preferably more than 100, preferentially more than 125, more preferably with 150 or more, and most preferably with from 150 to 200 theoretical plates. The reflux ratio (reflux amount to distillate withdrawal) is, depending on the number of stages realized and on the operating pressure, preferably less than or equal to 100, preferentially less than 70, more preferably from 30 to 60. The condensation may be carried out against cooling water or air. The distillate vessel is preferably designed as a liquid-liquid separator. As a result, any water present in the feed stream can be removed as the second phase in the distillate vessel and a technically water-free bottom product can be obtained.

The separation in i) is preferably carried out at a pressure of from 5 to 11 bara, preferably at a pressure of from 6 to 8 bara. The top temperature at which the separation is carried out is preferably from 35 to 65° C., preferentially from 45 to 50° C. When thermal integration is intended, it may be advantageous to carry out i) at higher temperature, and hence, higher pressure.

To heat the evaporator of the column, a customary heat transferrer, for example steam or warm water, and preferably waste heat from other processes, may be used. In the latter case, it may be advantageous to equip the column with more than one evaporator. The column is preferably equipped as a simple column with at least one evaporator and at least one condenser. Owing to the high energy requirements and the small temperature difference between bottom and top of the column, energy-saving connections are particularly preferred embodiments. Reference is made here by way of example to the method of vapor compression. A further particularly preferred connection is two-pressure connection (double effect distillation) in integration with a second column. The second column may preferably be a parallel-connected column with the same or different separation tasks. In this case, one of the columns is operated at such high pressure that its condensation temperature is sufficient to heat the other column. In the connection of columns with different separation tasks for heating purposes, it is possible in principle to connect any suitable column from the inventive process, but also a column which is present at the plant location outside the inventive process, with the inventive column of process i). More preferably, the second column is the $C_4$ separation column from c). In this case, one of the columns is operated at such high pressure that its condensation temperature is sufficient to heat the other column.

In a further preferred embodiment, low boilers are removed as the top product in a first distillation column; in the bottom of the column, a mixture comprising mainly 1-butene and isobutane is obtained. In a second column, this bottoms mixture is separated into 1-butene, which is obtained as the bottom product, and an isobutane-rich fraction (top product).

Pure 1-butene prepared by the inventive process comprises preferably less than 5000 ppmw (ppm by mass), preferably less than 2000 ppmw and more preferably less than 1500 ppmw of isobutene, and is a sought-after intermediate. It is used, for example, as a comonomer in the preparation of polyethylene (LLDPE or HDPE) and the preparation of ethylene-propylene copolymers. Pure 1-butene also finds use as an alkylating agent and is the starting material for the preparation of butan-2-ol, butene oxide, and valeraldehyde. A further use of the virtually isobutene-free 1-butene, prepared in accordance with the invention, is the preparation of n-butene oligomers, in particular by the Octol process.

In i), an isobutane-rich fraction is typically obtained in addition to the 1-butene (depending on the starting composition of the $C_4$ hydrocarbons). The isobutene-rich fraction can be purified further, preferably to pure isobutane. Purification to give pure isobutane can be effected, for example, by full hydrogenation of the alkenes still present to alkanes and subsequent distillation. The isobutane obtained in the workup has preferably a purity of at least 90% by mass of isobutane, more preferably 95% by mass of isobutane, and contains preferably less than 1000 ppmw, more preferably less than 200 ppmw, of olefins.

Feedstocks

In the inventive process, all technical $C_4$ hydrocarbon mixtures typically available may be used. Suitable isobutenic $C_4$ streams are, for example, $C_4$ fractions from crackers (for example steamcrackers, hydrocrackers, catcrackers), mixtures from Fischer-Tropsch syntheses, mixtures from the dehydrogenation of butanes, mixtures from skeletal isomerization of linear butenes and mixtures formed by metathesis of olefins. These techniques are described in the technical literature (K. Weissermel, H. J. Arpe, Industrielle Organische Chemie, Wiley-VCH, 5th edition, 1998, page 23-24; 65-99; 122-124).

Preference is given to using $C_4$ fractions from steamcrackers which are operated primarily for the production of ethene and propene and in which the raw materials used are, for example, refinery gases, naphtha, gas oil, LPG (liquefied petroleum gas) and NGL (natural gas liquid), or catcrackers. The $C_4$ cuts obtained as a by-product comprise, depending on the cracking process, different amounts of isobutene. Further main constituents are 1,3-butadiene, 1-butene, c-2-butene, t-2-butene, n-butane and i-butane. Typical isobutene contents in the $C_4$ fraction are from 18 to 35% by mass, in the case of $C_4$ fractions from steamcrackers, from 10 to 20% by mass in the case of fluid catcrackers (FCC).

For the inventive process, it is advantageous to remove polyunsaturated hydrocarbons, such as 1,3-butadiene, from the use mixture. Removal of the polyunsaturated hydrocarbons can be acheived by known processes, for example by extraction, extractive distillation or complex formation (cf. K. Weissermel, H. J. Arpe, Industrielle Organische Chemie, Wiley-VCH, 5th edition, 1998, pages 119 to 121).

One alternative to the removal of the polyunsaturated hydrocarbons is a selective chemical conversion. For example, 1,3-butadiene can be hydrogenated selectively to linear butenes, as described, for example, in EP 0 523 482. It is also possible to remove the 1,3-butadiene, at least partly, by selective conversions of the 1,3-butadiene, for example dimerization to cyclooctadiene, trimerization to cyclododecatriene, polymerization or telomerization reactions. When a crack-$C_4$ cut was used as the raw material, a hydrocarbon mixture (raffinate I or hydrogenated crack-$C_4$ (HCC$_4$))

always remains and comprises mainly the saturated hydrocarbons, n-butane and isobutane and the olefins isobutene, 1-butene and 2-butenes.

In the inventive process, in an additional purification stage which is connected upstream of one or more of a), b), c), d), e) or f), polyunsaturated hydrocarbons present in the $C_4$ hydrocarbon streams are preferably catalytically and selectively hydrogenated. More preferably, such a purification stage is provided at least before a) or c), and most preferably before c), especially when it cannot be ruled out that the technical $C_4$ hydrocarbon streams used comprise polyunsaturated hydrocarbons.

The polyunsaturated hydrocarbons are mainly 1,3-butadiene; 1,2-butadiene, butenine and 1-butene are present, if at all, in a significantly smaller amount. The hydrogenation can be effected in a one-stage or multistage hydrogenation process in the liquid phase over a palladium catalyst. To lower the content of 1,3-butadiene below preferably 1000 ppmw, a moderator which increases the selectivity of the palladium catalyst is added in the last stage of the hydrogenation. The moderator used is preferably carbon monoxide which is added in a fraction of from 0.05 to 100 ppm by mass (ppmw). The content of polyunsaturated hydrocarbons in the feed to this stage should be below 1%, preferably below 0.5%. In the literature, this type of selective hydrogenation of residual contents of 1,3-butadiene is known under the name SHP (selective hydrogenation process) (cf. EP 0 081 041; Erdol, Kohle, Erdgas, Petrochem. 1986, 39, 73).

When amounts of more than 1% of polyunsaturated hydrocarbons such as 1,3-butadiene are present in the isobutenic $C_4$ streams, they are preferably converted in upstream hydrogenations. These hydrogenations are preferably carried out in the liquid phase over a palladium catalyst. Depending on the content of unsaturated hydrocarbons, the hydrogenation may be carried out in a plurality of stages. For the conversion of crack-$C_4$ from a steamcracker with a content of 1,3-butadiene of typically from 38 to 45%, a two-stage version of the hydrogenation has been found to be useful. In this case, individual or all stages may be equipped with partial product recycling. In the effluent, concentrations of 1,3-butadiene of less than 1% are thus obtainable, so that a further conversion can be effected in a selective hydrogenation (SHP).

The hydrocarbon mixtures with isobutene and linear butenes used in the inventive process preferably have the following compositions, a hydrogenation or selective hydrogenation being carried out before one of a) to d), preferably before a) or c), depending on the content of unsaturated hydrocarbons.

TABLE 1

Typical compositions of technical hydrocarbon mixtures which can be used in the inventive process.

| Component | Steamcracker | | Steamcracker | | Catcracker | |
|---|---|---|---|---|---|---|
| | $HCC_4$ | $HCC_4/$ SHP | Raff. I | Raff. I/SHP | $CC_4$ | $CC_4/$ SHP |
| Isobutane [% by mass] | 1-4.5 | 1-4.5 | 1.5-8 | 1.5-8 | 36-37 | 36-37 |
| n-Butane [% by mass] | 5-8 | 5-8 | 6-15 | 6-15 | 12-14 | 12-14 |
| trans-Butene [% by mass] | 18-21 | 18-21 | 7-10 | 7-10 | 11-13 | 11-13 |
| 1-Butene [% by mass] | 35-45 | 35-45 | 15-35 | 15-35 | 11-13 | 11-13 |
| Isobutene | 22-28 | 22-28 | 33-50 | 33-50 | 14-16 | 14-16 |
| cis-Butene [% by mass] | 5-9 | 5-9 | 4-8 | 4-8 | 10-12 | 10-12 |
| 1,3-Butadiene [ppmw] | 500-8000 | 0-50 | 50-8000 | 0-50 | <10000 | 0-50 |

Explanation
$HCC_4$: typical of a $C_4$ mixture which is obtained from the crack-$C_4$ of a steamcracker (high severity) after the hydrogenation of the 1,3-butadiene without additional moderation of the catalyst.
$HCC_4$/SHP: $HCC_4$ composition in which residues of 1,3-butadiene have been reduced further in an SHP.
Raff. I (raffinate I): typical of a $C_4$ mixture which is obtained from the crack-$C_4$ of a steamcracker (high severity) after the removal of the 1,3-butadiene, for example by an NMP extractive rectification.
Raff. I/ SHP: Raff. I composition in which residues of 1,3-butadiene have been reduced further in an SHP.
$CC_4$: typical composition of a crack-$C_4$ which is obtained from a catcracker.
$CC_4$/SHP: $CC_4$ composition in which residues of 1,3-butadiene have been reduced further in an SHP.

Among others, the raffinate I or $HCC_4$ is an isobutenic hydrocarbon mixture preferably employed within the context of this invention. Since plants for working up $C_4$ hydrocarbons are generally constructed as a strand (integrated system of a plurality of plants), it is, however, possible that the raffinate I or $HCC_4$ passes through one or more other process stage(s) before entry into the inventive process. This process stage or these process stages may, for example, also be a process or process step(s) as have been described in the embodiments for a). $C_4$ hydrocarbon mixtures usable in the inventive process may also be those as obtained from processes as per the embodiments of a) and subsequent separation as per b). In particular, those mixtures as obtained in the preparation of tert-butanol (TBA) from isobutene after removal of the TBA may also be used. In this way, an individually adapted overall concept for workup with the appropriate product portfolio can be realized in each case.

Typical processes which can be connected upstream of the inventive processes are water scrubbings, purification processes in adsorbers, drying processes and distillations.

Water Scrubbing

A water scrubbing can fully or partly remove hydrophilic components, for example nitrogen components, from the technical hydrocarbon mixture comprising isobutene and linear butenes. Examples of nitrogen components are acetonitrile or n-methylpyrrolidone (which can stem, for example, from a 1,3-butadiene extractive distillation). Oxygen compounds (for example acetone from FCC) may also be removed partly by means of a water scrubbing. After a water scrubbing, the isobutenic hydrocarbon stream is saturated with water. In order to avoid biphasicity in the downstream process steps in the reactor, the reaction temperature there should be approx. 110° C. above the temperature of the water scrubbing.

Adsorber

Adsorbers are used to remove impurities. This may be advantageous, for example, when noble metal catalysts are used in one of the process steps. Often, nitrogen or sulfur compounds are removed by means of upstream adsorbers. Examples of adsorbents are aluminas, molecular sieves, zeolites, activated carbon, aluminas impregnated with metals. Adsorbents are sold by various companies, for example Alcoa (Selexsorb®).

Drying

Any water present in the isobutenic hydrocarbon mixture, which may stem, for example, from the water scrubbing, can be removed by known processes for drying. Suitable processes are, for example, the distillative removal of the water as an azeotrope. Often, an azeotrope containing $C_4$ hydrocarbons may be utilized or azeotroping agents may be added.

The drying of the hydrocarbon mixture may be advantageous for various reasons, for example to reduce the formation of alcohols (mainly tert-butyl alcohol) in a) or to avoid technical problems as a result of separation of water or to prevent ice formation at low temperatures (for example in the course of intermediate storage).

Distillation

Distillation steps may be utilized, for example, to remove impurities (for example low boilers such as $C_3$ hydrocarbons, high boilers such as $C_5$ hydrocarbons) or to obtain fractions with different isobutene concentrations. This can be done either directly with the raffinate I or the $HCC_4$ or after one or more other process stage(s) has/have been passed through. Direct distillation of the raffinate I, or of the $HCC_4$, makes it possible, for example, to separate into a relatively isobutene-rich fraction depleted in 2-butenes and n-butane.

Depending on the composition of the technical hydrocarbon mixture to be used and/or on the purities of the target products, the technical hydrocarbon mixture may thus be used directly in a) of the inventive process or else only after a pretreatment by one or more of the aforementioned processes.

The inventive process can be used in a simple manner to prepare ETBE, or a composition which contains ETBE, and is obtained as the bottom product of the reactive distillations or of the distillations in b) and e), preferably as the bottom product of b).

An inventive composition comprising ETBE, which can be prepared, for example, with the inventive process's and which is preferably obtained as the bottom product II in b), comprises greater than or equal to 90 parts by mass of ETBE, from 0 to 7 parts by mass, preferably from 0 to 5 parts by mass, of ethanol, from 0 to 3 parts by mass, preferably from 0 to 2.5 parts by mass, of tert-butanol, less than or equal to 2 parts by mass, preferably less than or equal to 1.5 parts by mass, of hydrocarbons having a number of carbon atoms greater than or equal to 5, and less than or equal to 1 part by mass of hydrocarbons having a number of carbon atoms of 4. Such a composition can be obtained, for example, by the process according to the invention. It may be advantageous that the inventive composition comprise a maximum of from $1 \times 10^{-4}$ to $1000 \times 10^{-4}$ parts by mass of diethyl ether. The inventive composition preferably does not have any heterogeneous water. The inventive composition more preferably has less than 0.05 part by mass of water. The inventive composition more preferably has greater than or equal to 90 parts by mass, in particular from 90 to 97.5 parts by mass, of ETBE, from 1 to 5 parts by mass of ethanol, from 0.5 to 1 part by mass of tert-butanol, from 0.5 to 1 part by mass of hydrocarbons having a number of carbon atoms greater than or equal to 5, from 0.1 to 0.5 part by mass of hydrocarbons having a number of carbon atoms of 4, and from 0 to 0.05 part by mass, in particular from 0.0001 to 0.01 part by mass of water. The parts by mass specified for the compositions according to the invention are more preferably percentages by mass.

The inventive ETBE may be used as a fuel or fuel additive. Since bioethanol, i.e. ethanol which has been obtained from renewable raw materials, can be used to prepare the inventive ETBE, the inventive process can make a contribution to the protection of fossil fuel reserves. In addition to ETBE, a 1-butenic stream is obtained in the process according to the invention and can be worked up to give 1-butene which is used, for example, as a comonomer in the preparation of polymers.

EXAMPLES

The present invention is described by way of example in the Examples hereinafter. Obviously, numerous modifications and variations of the present invention are possible in light of the above teachings. It is therefore to be understood that, within the scope of the appended claims, the invention may be practiced otherwise than as specifically described herein.

The example calculations which follow were carried out with the simulation program ASPEN Plus. In order to obtain transparent, reproducible data, only generally available substance data were used. The use of kinetic approaches was deliberately dispensed with. In addition, the use of a reactive distillation was dispensed with in all variants. These simplifications make it possible for the person skilled in the art to easily comprehend the calculations. Although the methods used do not have sufficient precision for the design of industrial plants, the qualitative differences in the arrangements are detected correctly. In all variants shown, the isobutene conversion can be increased by use of one or more reactive distillation(s).

The reactors and ETBE columns were calculated with the "UNIFAC-DMD" property method. For the calculation of the $C_4$ columns, an equation of state was used with the "Peng-Robinson" property method. The following assumptions were made:

All reactors attain the equilibrium calculated with UNIFAC fully at 50° C.

The ETBE columns were calculated with a reflux ratio of 0.8. For the $C_4$ columns, the desired purities of the target fractions were used as prerequisites for the simulations.

In the ETBE columns, a $C_4$/ethanol azeotrope was removed via the top. The EtOH was scrubbed out with water in extractors which were modelled as simple component splitters.

The EtOH-water mixture obtained from the extractors was worked up by distillation in a further column which has not been shown in the connection diagrams. Both products of the K-EtOH were, if appropriate after suitable drying of the ethanol, recirculated into the process.

The basis of the calculated examples was a raw material mix of typical $C_4$ raw materials obtainable on the market. The raw material stream of 10 t/h comprises 28% by mass of isobutene and 35% by mass of 1-butene.

From this stream, the isobutene should be converted virtually fully to an ETBE product with an ethanol content of approx. 5% by mass. In addition, the isobutene should be removed chemically by the ETBE synthesis to such an extent that a 1-butene product can be prepared in an amount of 3 t/h with a purity greater than 99.5%. This corresponds to a 1-butene yield of approx. 85%. In the 1-butene product, a maximum of 2000 ppm of isobutene should be present. In Table 2, the composition of the $C_4$ raw material stream is compared to the desired specification of the 1-butene obtained as a by-product. The amount of ethanol used was from 2426 to 2545 kg/h (i.e. from 5 to 11% molar excess, see below) with a water content of 1% by mass.

TABLE 2

Composition of the C$_4$ raw material stream
and 1-butene specification (in % by mass)

|  | C$_4$-Feed | | 1-Butene | |
|---|---|---|---|---|
| Components | [kg/h] | [%] | [kg/h] | [%] |
| Isobutane | 500 | 5.0 | 3 | 0.2 |
| 1-Butene | 3500 | 35.0 | 2990 | 99.5 |
| cis-2-Butene | 1400 | 14.0 |  | 0.0 |
| trans-2-Butene | 800 | 8.0 |  | 0.0 |
| Isobutene | 2800 | 28.0 | 6 | 0.2 |
| n-Butane | 1000 | 10.0 | 1 | 0.1 |
| Total | 10000 | 100 | 3000 | 100 |

Three process variants of different suitability for achieving the objective have been calculated below.

The simplest variant A was a one-stage process which was intended to serve as a comparison. According to FIG. 6, ethanol and isobutene are reacted in a reaction stage R-a up to equilibrium. In the distillation stage K-b1, the ETBE was removed as the bottom product (II). The column had 50 theoretical plates and was operated at a reflux ratio of 0.8. The distillate of this column was a C$_4$/EtOH azeotrope from which the ethanol was scrubbed out, for example with water, in an extraction column K-f2. The raffinate of the extraction column K-f2 was fed to a C$_4$ column K-c1 in which isobutane, isobutene and 1-butene were removed via the top. The distillate IV of the K-c1 was passed directly into a further column K-i1 in which principally isobutane was removed via the top. The top product obtained was a 1-butene-rich fraction which comprised the majority of the isobutene unconverted in R-a.

The 1-butene prepared by variant A comprised 1.91% isobutene, see table 3, and thus did not achieve the target of 2000 ppm. Moreover, the molar ethanol excess in the feed of R-a in variant A was restricted to about 5% (2426 kg/h in the example), since the excess EtOH could be removed as an azeotrope only in the top of column K-b1. Thus, 5.2% EtOH was already found in the ETBE product. 5113 kg/h of ETBE product having a purity of 93.6% were formed.

A process improvement was investigated as variant B and is shown in FIG. 7. In order to drive the equilibrium further in the ETBE direction, a further reactor R-b2 was connected downstream of column K-b1 and reacted the residual isobutene with the ethanol removed via the top as azeotrope D-b1 in K-b1. To increase the conversion, a further EtOH stream of 200 kg/h was fed to the reactor. The ETBE formed in addition compared to variant A was removed in a further C$_4$-/ETBE distillation K-b3. The entire C$_4$ stream had to be distilled via the top for a second time, i.e. the energy demand of K-b3 was virtually just as great as that of K-b1. Subsequently, the extraction K-f2 and the 1-butene distillation K-c1 and K-i1 were passed through as in variant A. The 1-butene product with less than 2000 ppm of isobutene then just achieved the required product specification. Owing to the higher isobutene conversion, 5340 kg/h of ETBE product (variant A: 5113 kg/h) with a purity of 93.7% were formed. The total energy demand of the plant was, however, about 13% higher compared to variant A.

In the process according to the invention variant C according to FIG. 8, a second reaction, distillation and extraction stage R-d1, K-e1 and K-h2 was connected to a second EtOH supply as under variant B, between the two C$_4$ columns K-c1 and K-i1. This had the advantage that the greater portions of the feed III of K-c1 were obtained as the bottom product V and only the portion of the C$_4$ stream which was to be worked up to pure 1-butene in K-i1 was distilled for a second time. In the present case, the energy requirement of K-f2 in variant B was more than twice as high as the energy demand of K-e1 in variant C. A disadvantage of variant C was that a second extraction column K-h2 had to be provided. Since the throughput through R-d1, K-e1 and K-h2 was, though, less than half of the throughput through K-b3 in variant B, the total capital costs were correspondingly lower.

The amount of isobutene in the 1-butene product was significantly less than 2000 ppm in the example calculated. When the stream VII was recycled into a), the amount and composition of the ETBE product obtained were very similar to variant B.

Table 3 shows the conversions achieved in the three variants. While variant A clearly did not meet the required quality of the 1-butene product, an on-spec by-product was calculated in the two two-stage processes B and C. The increased isobutene conversion was achieved in both variants by virtue of distillative removal of the ETBE reaction product before a second reaction stage and hence by virtue of increased energy input. The inventive arrangement of the second reaction stage in variant C between the two C$_4$ columns K-c1 and K-c2, however, reduced the amount of the stream to be distilled additionally to less than half. This led to distinct savings in energy demand and investment.

TABLE 3

Conversions and 1-butene qualities of the three variants

|  | Variant A, one-stage | Variant B, two-stage | Variant C, two-stage |
|---|---|---|---|
| Isobutene in the feed [kg/h] | 2800 | 2800 | 2800 |
| Ethanol feed (net) [kg/h] | 2426 | 2545 | 2548 |
| Isobutene after stage 1 [kg/h] | 133.1 | 149.1 | 149.1 |
| Stage 1 conversion [%] | 95.2 | 94.7 | 94.7 |
| Isobutene after stage 2 [kg/h] |  | 6.6 | 5.6 |
| Stage 2 conversion [%] |  | 95.6 | 96.2 |
| Total conversion [%] | 95.2 | 99.8 | 99.8 |
| Isobutene in the 1-butene [ppm] | 19130 | 1957 | 1833 |
| 1-Butene purity [%] | 97.8 | 99.5 | 99.5 |

Table 4 compares the calculated energy demands of all three variants. In all three arrangements, the energy demand of columns K-b1, K-c1 and K-i1 was virtually identical. Although variant A had the lowest total energy demand, the product specification was not met. In variant B, double the amount of C$_4$ had to be distilled via the top in the ETBE portion, and its energy demand was therefore 13% higher than in variant A. In contrast, variant C showed a way of achieving the required isobutene conversion with an energy demand increased by only 6%.

TABLE 4

Energy demand of the three variants

|  | Variant A, one stage | Variant B, two stage | Variant C, two stage |
|---|---|---|---|
| Q K-b1 [kW] | 1284 | 1287 | 1287 |
| Q K-EtOH [kW] | 126 | 122 | 155 |
| Q K-b3 [kW] |  | 1267 |  |
| Q K-c1 [kW] | 3510 | 3501 | 3580 |
| Q K-e1 [kW] |  |  | 593 |
| Q K-i1 [kW] | 3813 | 3680 | 3674 |
| Total Q [kW] | 8733 | 9857 | 9289 |
| Increased demand ΔQ compared to variant A [%] | 0 | 12.9 | 6.4 |

Table 5 shows the calculated ETBE qualities, as can be obtained with variants A, B and C.

TABLE 5

ETBE qualities of the three variants:

|  | Variant A, one stage | Variant B, two stage | Variant C, two stage |
|---|---|---|---|
| Ethanol feed (total) [kg/h] | 2426 | 2545 | 2548 |
| Molar EtOH excess in % | 5.5 | 10.7 | 10.8 |
| EtOH in the ETBE [% by mass] | 5.2 | 5.0 | 5.1 |
| ETBE in the ETBE [% by mass] | 93.6 | 93.8 | 93.8 |
| Amount of ETBE [kg/h] | 5113 | 5340 | 5318 |

Table 5 shows that similar qualities of ETBE were obtainable with variants A, B and C, although the quality of the ETBE according to variant A with regard to the ethanol content and the ETBE content was in each case higher and lower respectively than for variants B and C and hence poorer. Since variant A, as can be taken from table 3, additionally also afforded only relatively contaminated 1-butene as a by-product, variants B or C are preferable in spite of the higher energy demand. It can be taken from the results listed in table 4 that the inventive variant C had a distinctly lower heat demand than variant B and hence constitutes the energetically most favorable variant in relation to the quality of ETBE and 1-butene.

The designations in the figures FIG. 1 to FIG. 8 have the following meanings:

| | |
|---|---|
| (a) | partial isobutene conversion to products |
| (b) | separation of the product from (a) into a fraction II comprising ETBE and C$_4$ hydrocarbons III |
| (c) | distillative separation of III into IV and V |
| (d) | etherification of isobutene with ethanol VI |
| (e) | removal of an ETBE-containing stream VII |
| (i) | 1-butene removal |
| I | technical mixture of C$_4$ hydrocarbons |
| II | fraction comprising ETBE |
| III | remaining C$_4$ hydrocarbons |
| IV | 1-butene and isobutene-containing fraction |
| V | isobutene-free fraction comprising 2-butenes and n-butanes |
| VI | ethanol |
| VII | ETBE-containing stream |
| VIII | C$_4$ hydrocarbons from stage e) or h) |
| D-b1 | distillate of K-b1 |
| D-b3 | distillate of K-b3 |
| D-c1 | aqueous phase from decanter of K-c1 |
| D-e1 | top product of K-e1 |
| D-i1 | K-i1 distillate, organic phase |
| D-i2 | low boilers |
| E-f1 | extractant inlet |
| E-f2 | extractant outlet |
| E-h1 | extractant inlet |
| E-h2 | extractant outlet |
| K-b1 | distillation |
| K-b3 | distillation |
| K-c1 | column for separating the C$_4$ hydrocarbons |
| K-e1 | column for removing the ether |
| K-f2 | extraction column |
| K-h2 | extraction column |
| K-i1 | column for 1-butene removal |
| K-i2 | column for isobutane removal |
| R-a | reactor |
| R-a1 | reactor |
| R-a2 | reactor |
| R-b2 | etherification reactor (comparative example) |
| R-d1 | etherification reactor |
| S-i1 | 1-butene |
| S-i2 | isobutane |
| W-b1 | Bottom evaporator |
| W-b2 | Condenser |
| W-b | Bottom evaporator |
| W-b4 | Condenser |
| W-c1 | Bottom evaporator |
| W-c2 | Condenser |
| W-e1 | Bottom evaporator |
| W-e2 | Condenser |
| W-i1 | Bottom evaporator |
| W-i2 | Condenser |
| W-i3 | Bottom evaporator |
| W-i4 | Condenser |

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out. Terms such as "contain(s)" and the like as used herein are open terms meaning 'including at least' unless otherwise specifically noted.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A process for preparing ethyl tert-butyl ether (ETBE) from a technical mixture of C$_4$ hydrocarbons I which comprises at least 1-butene, isobutene, n-butane and 2-butenes, comprising
  a) reacting a portion of the isobutene present in the technical mixture with ethanol in the presence of an acidic catalyst to give ETBE and unconverted C$_4$ hydrocarbons III,
  b) removing the unconverted C$_4$ hydrocarbons III from the effluent of a) by a thermal separating process to obtain a fraction II comprising ETBE,
  c) distillatively separating the C$_4$ hydrocarbons III into a fraction IV comprising at least 1-butene and isobutene, and a virtually isobutene-free fraction V comprising at least 2-butenes and n-butane,
  d) feeding fraction IV of c) directly into a reactor and with ethanol VI in the presence of an acidic catalyst to give ETBE and unconverted C$_4$ hydrocarbons VIII, and
  e) removing the unconverted C$_4$ hydrocarbons VIII from the effluent of d) to obtain a fraction VII comprising ETBE.

2. The process of claim 1, wherein the acid-catalyzed etherification in d) is carried out in at least one reaction stage, and wherein one reaction stage of the at least one reaction stage comprises a reactive distillation.

3. The process of claim 1, wherein the acid-catalyzed etherification in d) is carried out in at least two reaction stages, and wherein at least the last reaction stage of the at least two reaction stages comprises a reactive distillation.

4. The process of claim 3, wherein in d), the last reaction stage is carried out as a reactive distillation wherein e) is carried out.

5. The process of claim 1, wherein after e), the unconverted $C_4$ hydrocarbons VIII comprise a residual amount of ethanol, and wherein the residual amount of ethanol in the unconverted $C_4$ hydrocarbons VIII is scrubbed out in an extraction step with water.

6. The process of claim 1, wherein the acid-catalyzed etherification in a) comprises at least one reaction stage, and wherein a reaction stage of the at least one reaction stage comprises a reactive distillation.

7. The process of claim 6, wherein the acid-catalyzed etherification in a) comprises at least two reaction stages, and wherein at least the last reaction stage of the at least two reaction stages comprises a reactive distillation.

8. The process of claim 7, wherein in a), the last reaction stage comprises a reactive distillation wherein b) is carried out.

9. The process of claim 1, further comprising between b) and c), a process step f) wherein in f), the $C_4$ hydrocarbons III comprise a residual amount of ethanol, and wherein the ethanol is scrubbed out of the $C_4$ hydrocarbons III in an extraction step with water.

10. The process of claim 1, wherein a), b) or a) and b), comprise at least one reactor, and wherein a reactor of the at least one reactor is operated in loop mode.

11. The process of claim 1, wherein the 2-butenes present in at least one of the $C_4$ hydrocarbons I, III, and VIII are hydrogenated catalytically in at least one additional purification stage which is connected upstream of one or more of a), b), c) or d).

12. The process of claim 11, wherein the 2-butenes are hydrogenated in at least two reaction stages, and wherein at least the last reaction stage is carried out in the presence of from 0.05 to 100 ppmw of CO.

13. The process of claim 11, wherein the hydrogenation is carried out between b) and c).

14. The process of claim 1, wherein the reaction in a) is carried out such that the conversion of the portion of the isobutene is over 70%.

15. The process of claim 1, wherein the acidic catalyst used in the reactions of isobutene with ethanol is an ion exchange resin.

16. The process of claim 1, wherein the fraction VII optionally comprises unconverted ethanol, and wherein the fraction VII is recycled into a), b), or a) and b).

17. The process of claim 16, wherein the fraction VII comprises unconverted ethanol.

18. The process of claim 16, wherein the fraction VII is recycled into a).

19. The process of claim 16, wherein the fraction VII is recycled into b).

20. The process of claim 16, wherein the fraction VII is recycled into a) and b).

21. The process of claim 1, wherein a), d) or a) and d) comprise ethanol which comprises from 0.05 to 1% by mass of ETBE as a denaturing agent.

22. The process of claim 1, wherein the $C_4$ hydrocarbon fraction VIII obtained in e) is worked up to give 1-butene which comprises an isobutene content of less than 5000 ppmw.

* * * * *